Figure 1:
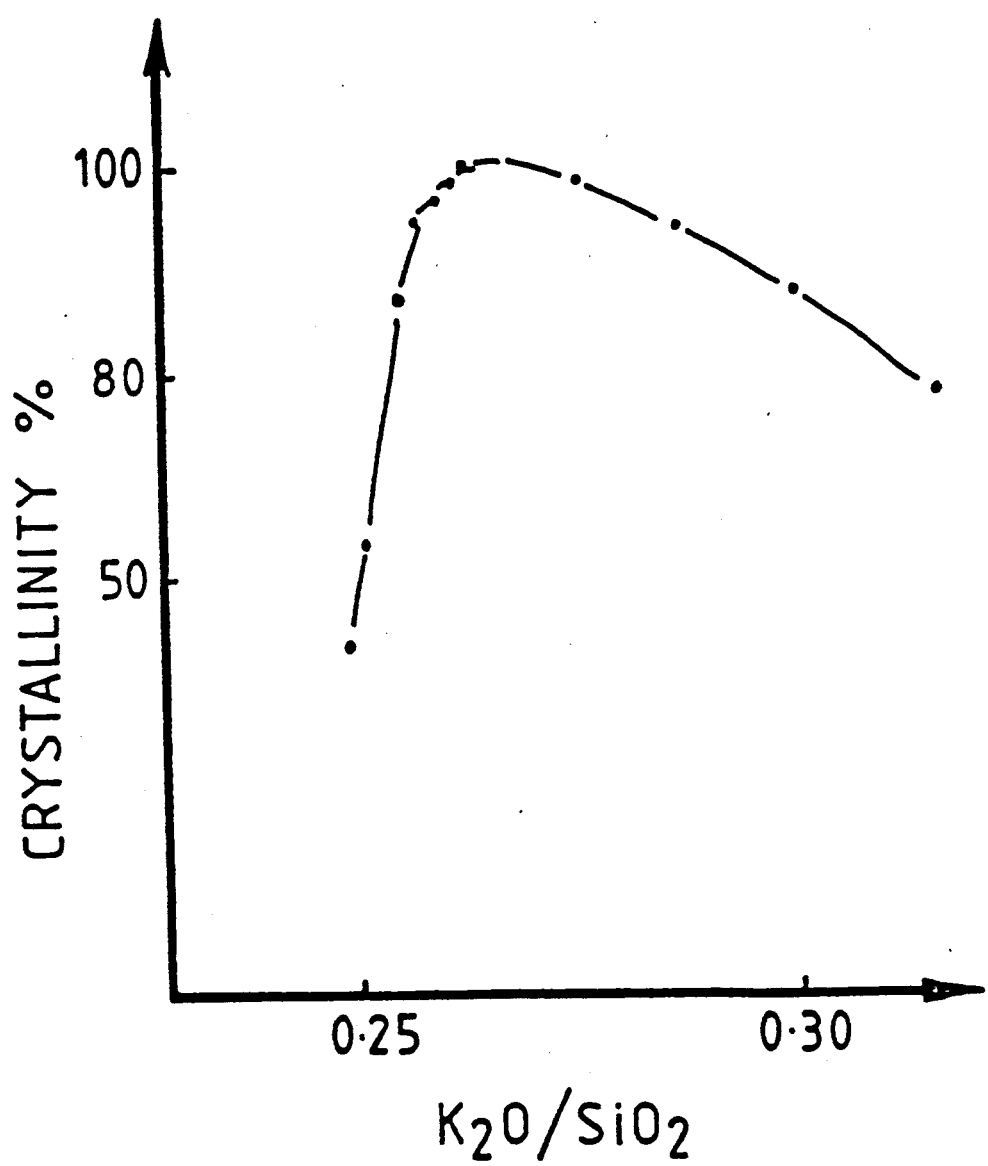

United States Patent [19]

Koetsier et al.

[11] Patent Number: 5,051,387

[45] Date of Patent: Sep. 24, 1991

[54] ZEOLITE L PREPARATION

[75] Inventors: Wicher T. Koetsier, Mijnsheerenland; Johannes P. Verduijn, Spijkenisse, both of Netherlands

[73] Assignee: Exxon Research & Engineering Company, Linden, N.J.

[21] Appl. No.: 440,150

[22] Filed: Nov. 22, 1989

Related U.S. Application Data

[62] Division of Ser. No. 175,477, Mar. 31, 1988, abandoned, which is a division of Ser. No. 808,414, Dec. 12, 1985, abandoned.

[30] Foreign Application Priority Data

Dec. 17, 1984 [GB] United Kingdom ............... 8431760

[51] Int. Cl.$^5$ .................. B01J 29/28; B01J 29/32; C10B 33/28
[52] U.S. Cl. .................................. 502/74; 423/328; 502/60
[58] Field of Search ..................... 502/60, 66, 74; 423/328, 329; 585/407, 449

[56] References Cited

U.S. PATENT DOCUMENTS 4,104,320  8/1978  Bernard et al. .................. 585/419
4,544,539 10/1985  Wortel ............................. 502/66

FOREIGN PATENT DOCUMENTS 142354  5/1985  European Pat. Off. ........... 502/60

Primary Examiner—Carl F. Dees
Attorney, Agent, or Firm—Edward F. Sherer

[57] ABSTRACT

Zeolite L with cylindrical morphology and having excellent properties as a catalyst base may be prepared with high crystallinity and reduced contamination even in large scale syntheses were fluctuation in gel compositions may occur by employing a gel composition having the following molar ratios of components:

2.64–2.67 $M_{2/n}O:Al_2O_3$:8.8–9.7 $SiO_2$:145–160 $H_2O$ where M is a cation of valence n, especially potassium. The ratio $M_{2/n}O:SiO_2$ is preferably at least 0.275.

8 Claims, 2 Drawing Sheets

ZEOLITE L PREPARATION

This is a division of application Ser. No. 175,477, filed Mar. 31, 1988 (now abandoned), which is a division of application Ser. No. 808,414, filed Dec. 12, 1985 (now abandoned).

This invention relates to the preparation of zeolite L, particularly of highly crystalline forms of zeolite L, as well as their use in catalysis, particularly for aromatization.

Zeolite L has been known for some time as an adsorbant, and in U.S. Pat. No. 3,216,789 is described as an aluminosilicate of the formula:

$$0.9-1.3\ M_{2/n}O:Al_2O_3:5.2-6.9\ SiO_2:yH_2O$$

(where M is an exchangeable cation of valence n and y is from 0 to 9) having a characteristic X-ray diffraction pattern. The preparation of zeolite L described in U.S. Pat. No. 3,216,789 comprises crystallizing the zeolite from a reaction mixture comprising mole ratios:

| | |
|---|---|
| $K_2O/(K_2O + Na_2O)$ | 0.33–1 |
| $(K_2O + Na_2O)/SiO_2$ | 0.35–0.5 |
| $SiO_2/Al_2O_3$ | 10–28 |
| $H_2O/(K_2O + Na_2O)$ | 15–41 |

The silica to alumina ratio in this reaction mixture is significantly higher than the ratio in the formed zeolite.

British Patent 1 202 511 describes a revised preparation using lower proportions of silica in the reaction mixture which comprises mole ratio of reactants as:

| | |
|---|---|
| $K_2O/(K_2O + Na_2O)$ | 0.7–1 |
| $(K_2O + Na_2O)/SiO_2$ | 0.23–0.35 |
| $SiO_2/Al_2O_3$ | 6.7–9.5 |
| $H_2O/(K_2O + Na_2O)$ | 10.5–50 |

The ratio $H_2O/(K_2O+Na_2O+SiO_2+Al_2O_3)$ is preferably not greater than 6 to give a "dry gel". Example 6 uses a crystallization gel having a composition: 2.75 $K_2O:Al_2O_3$ 8.75 $SiO_2:100H_2O$ and obtains zeolite L but no indication is given of the degree of crystallinity, the purity or morphology of the product. Furthermore, no indication is given that the product is useful catalytically, only that it is a zeolite of the molecular sieve type.

Frety et al in C R Acad Sc Paris, t275, Serie C-1215 describes the electron microscope examination of zeolite L in which particles were said to be observed in the for of slightly deformed cylinders with very variable dimensions GB 1 393 365 describes zeolite AG1, related to zeolite L, having the molar composition other than water:

$$1.05\pm 0.3\ M_2O:Al_2O_3:4.0-7.5\ SiO_2$$

wherein M is potassium or a mixture of potassium and sodium, and an X-ray powder diffraction pattern said to have discrepancies when compared with the zeolite L pattern.

Zeolite AG1 is described as being prepared by reacting at least one aluminium component, at least one silicon component and at least one alkali metal component, in an aqueous medium, the sole or major silicon component being a water glass having a molar ratio $SiO_2/M_2O$ of 3.5 to 4.0 to give a reaction mixture with oxide molar ratios in one of the following ranges:

| | |
|---|---|
| Range 1 | |
| $SiO_2/Al_2O_3$ | 7–14 |
| $(K_2O + Na_2O)/SiO_2$ | 0.25–0.85 |
| $K_2O/(K_2O + Na_2O)$ | 0.75–1.0 |
| $H_2O/(K_2O + Na_2O)$ | 25–160 |
| Range 2 | |
| $SiO_2/Al_2O_3$ | 14–20 |
| $(K_2O + Na_2O)/SiO_2$ | 0.25–0.85 |
| $K_2O/(K_2O + Na_2O)$ | 0.5–1.0 |
| $H_2O/(K_2O + Na_2O)$ | 25–160 |
| Range 3 | |
| $SiO_2/Al_2O_3$ | 20–40 |
| $(K_2O + Na_2O)/SiO_2$ | 0.25–1.0 |
| $K_2O/(K_2O + Na_2O)$ | 0.4–1.0 |
| $H_2O/(K_2O + Na_2O)$ | 25–160 |

It is indicated that at $(K_2O+Na_2O)/SiO_2$ approaching the maximum of 0.85 in Range 2 the product may be contaminated with phillipsite. Example 10 uses a reaction mixture of the composition: 2.71 $M_2O:Al_2O_3:8.75\ SiO_2:84\ H_2O$ where $M_2O$ is 0.8 $K_2O+0.2\ Na_2O$. The product obtained is zeolite AG1 but no indication is given of the degree of crystallinity, the morphology or the purity of that product or of its catalytic performance.

EP 96479 describes and claims zeolite L having a characteristic morphology and size, which is particularly valuable for use as a catalyst base in hydrocarbon conversions such as aromatization. This zeolite has an X-ray diffraction (XRD) pattern obtained with CuKα radiation having the following significant d (Å) values:

TABLE A

| |
|---|
| 16.1 ± 0.4 |
| 7.52 ± 0.05 |
| 6.00 ± 0.04 |
| 4.57 ± 0.04 |
| 4.35 ± 0.04 |
| 3.91 ± 0.02 |
| 3.47 ± 0.02 |
| 3.28 ± 0.02 |
| 3.17 ± 0.02 |
| 3.07 ± 0.02 |
| 2.91 ± 0.02 |
| 2.65 ± 0.02 |
| 2.46 ± 0.02 |
| 2.42 ± 0.01 |
| 2.19 ± 0.01 | and comprising crystallites in the form of cylinders with a mean diameter of at least 0.1 micron, preferably at least 0.5 micron. The above XRD lines characterize the zeolite of the invention and correspond to those identified as characteristic of zeolite L in U.S. 3,216,789. In general the ten most prominent peaks in the XRD pattern of the materials of the invention are given in Table B below:

TABLE B

| |
|---|
| 16.1 ± 0.4 |
| 4.57 ± 0.04 |
| 3.91 ± 0.02 |
| 3.66 ± 0.02 |
| 3.47 ± 0.02 |
| 3.28 ± 0.02 |
| 3.17 ± 0.02 |
| 3.07 ± 0.02 |
| 2.91 ± 0.02 |

| TABLE B-continued |
| --- |
| 2.65 ± 0.02 |

The disclosure of EP 96479 is incorporated herein by reference.

As indicated in EP 96479, it is preferred that the synthesis of the zeolite there described is conducted so that the amount of the contaminant zeolite W, which is known to grow in such a system as a competitive phase, is minimised. A preferred synthesis gel described in EP has the following mole ratios:

$$2.62 K_2O:Al_2O_3:10SiO_2:160H_2O$$

and it is discussed how this gel may be varied by changing the molar amount of one component within the following ranges:

| | |
| --- | --- |
| $K_2O$: | 2.4–3.0 moles |
| $Al_2O_3$: | 0.6–1.3 moles |
| $SiO_2$: | 8–12 moles |
| $H_2O$: | 120–240 moles |

It is indicated that decresing the amount within that range tends to increase zeolite W contamination nation while increasing the amount of $K_2O$ tends to produce a clam-shaped product rather than the desired cylindrical morphology. In addition it is stated that decreasing the amount of $K_2O$ will result in amorphous material.

Zeolite L may be used as a catalyst base in aromatization reactions. U.S. Pat. No. 4,104,320 discloses dehydrocyclization of aliphatic compounds in the presence of hydrogen using a catalyst comprising zeolite L and a group VIII metal. The particular zeolite disclosed in EP 96479 is remarkably effective in such aromatization reaction being capable of forming catalysts which have extended lifetime.

However, only EP 96479 describes the preparation of zeolite L with cylindrical morphology which had this improved lifetime performance, and a problem encountered with that preparation is that minor variations in gel composition, within the tolerances of large scale production, can result in poorer product with decreased crystallinity and/or less well defined cylindrical morphology and/or increased contamination by other zeolites such as W and/or amorphous phases.

It has now been found that by operating within a particularly narrowly defined range of synthesis gel parameters, obtained by varying the gel composition, against the teaching of the art, a highly crystalline cylindrical zeolite as described in EP 96479 (which has been found to be more highly crystalline than any zeolite L prepared by other prior art processes) may be prepared with a reduced tendency to form zeolite W as contaminant and also with less amorphous phase. Moreover, the process is less susceptible to the formation of undesirable contaminants as a result of variations in the synthesis gel which may arise e.g. through fluctuations in the mixing of the ingredients, in particular on an industrial scale.

Accordingly in one aspect this invention provides a process for the preparation of zeolite L comprising cylindrical crystallites with an aspect ratio (ratio of length the curved cylindrical side in the axial direction to the cylinder diameter) of at least 0.4, preferably at least 0.5, in which an alkaline reaction mixture comprising water, a source of silicon and a source of aluminium with a composition having the following molar ratios (expressed as oxides):

$$2.63-2.67\ M_{2/n}O:Al_2O_3:8.8-9.7\ SiO_2 145-160\ H_2O$$

(where M is a cation of valence n or a mixture of cations, and is preferably potassium) preferably with the molar ratio of $M_{2/n}O/SiO_2$ being at least 0.275 (more preferably 0.275–0.30), is heated to a temperature of at least 75° C., and preferably from 100° C. to 250° C., more preferably from 120° C. to 225° C. to form the desired zeolite L product.

The zeolites of the invention are preferably aluminosilicates and will be described hereinafter in terms of aluminosilicates, though other elemental substitutions are possible, for example aluminium may be substituted by gallium, boron, iron and similar trivalent elements, and silicon may be substituted by elements such as germanium or phosphorus. The aluminosilicates preferably have a composition (expressed in terms of molar ratios of the constituent oxides in anhydrous form) of:

$$(0.9-1.3)\ M_{2/n}O:Al_2O_3:xSiO_2 \qquad (I)$$

wherein M is a cation of valence n, x is from 5 to 7.5, preferably from about 5.7 to about 7.4. The zeolitic materials of the invention have high crystallinity as shown by a well-defined X-ray diffraction pattern (without binder or other diluents present) with sharp peaks. Crystallinity may be measured, conveniently as the potassium form (zeolite KL) relative to a quartz standard by comparing the peak areas for the reflection from the 220 plane (d=4.57±0.04 Å) and the 221 plane (d=3.91±0.02) for the zeolitic material of the invention with the peak area for the from the 110 plane (d=2.46±0.02) of the quartz. The ratio of the combined peak areas of the 220 and 221 reflections of the zeolitic material to the peak area of the 110 reflection of quartz is a measure of the crystallinity of the sample. To provide a comparison between different samples and to eliminate cation effects the peak area determination is preferably carried out on the same cation form of the zeolite, and preferably the potassium form was chosen.

The exchangeable cation M is very preferably potassium, but it is possible for a part of M to be replaced by other cations such as alkali and alkaline earth metals for example sodium, rubidium or caesium.

In general formula I x (the mole ratio $SiO_2:Al_2O_3$) is more preferably from about 6 tc about 7 and most preferably from about 6.0 to about 6.5.

The zeolite prepared by the invention may be hydrated, typically with from 0 to 9 moles of water per mole of $Al_2O_3$. When used as a catalyst base, as described hereinafter, the zeolite of the invention is preferably first calcined to remove water. In normal preparation from aqueous gels a hydrated form is first prepared and this may be dehydrated by heating.

Scanning electron micrographs (SEM) of the materials of the invention show these to have very distinct crystal morphology. The zeolite produced by this invention appear as distinct cylinders in scanning electron micrographs, as described in EP 96479. The terms "cylinder" and "cylindrical" are used herein to describe particles having substantially the shape of a cylinder as defined in solid geometry—that is, a solid bounded by a surface generated by a line moving parallel at a distance r to a fixed line so as to cut a fixed plane curve and by two basal surfaces which cut the fixed line, these basal surfaces preferably being substantially parallel planes (bases) which intersect the fixed line. The aspect ratio is defined as the ratio of the length of the plane curve in the direction of the fixed line to 2r. The cylindrical particles of the invention are preferably well-defined circular cylinders (circular cross-section) and most preferably substantially in the form of right circular cylinders (wherein the bases are normal to the cylinder axis).

Cylindrical particles have been shown in EP 96479 to have excellent properties of extending catalyst life when used as catalyst bases for aromatization catalysts. This is in contrast to other morphologies, and in particular particles with cylindrical morphology have been shown better than particles with a clam-like shape. The term "clam" is used to describe particles having two generally convex faces joined to give the appearance of a clam shell. The zeolites prepared by the invention are preferably characterized by at least 50%, more preferably 70% and most preferably 85%, of the crystallites being cylinders. The aspect ratio of the cylindrical crystallites is preferably from 0.5 to 1.5. It is an important aspect of the invention that it provides a means of preparing cylindrical particles having the property of extending catalyst life as described above. As shown in the Comparative Examples herein and in EP 96479 prior art processes are not effective at preparing the same distinct cylindrical morphology.

A further particularly surprising feature of the invention is that large crystallites wherein the mean diameter of the cylinders is at least 0.1 micron may be prepared. The cylindrical particles preferably have a mean diameter of at least 0.5 micron, and more preferably 0.7 micron this invention provides zeolites comprising these large cylindrical crystallites. The crystallites are more preferably from 0.5 to 4 micron, and most preferably from 1.0 to 3.0 micron. Transmission electron diffraction indicate these are single crystals rather than agglomerates. It is a further surprising feature of the invention that the zeolite with cylindrical morphology may be prepared by controlling the composition of the reaction mixture within certain limits, depending upon the aspect ratio required, and that by operating within these limits it is possible to obtain relatively large cylindrical particles in a narrow size distribution.

This invention is concerned with further improvement in the preparation of cylindrical particles over the process described in EP 96479. particularly to reduce the susceptibility to the formation of zeolite W (even under conditions where the synthesis gel is contaminated with seeds for zeolite W) and to provide a process which is less susceptible to fluctuations in gel composition, which are unavoidable in large scale preparations.

To achieve this a specific narrow gel composition range is required.

There are four principle components to the reaction mixture or synthesis gel and thus generally:
aluminium
silicon
potassium (optionally with up to 30 mole% replaced by alkali or alkaline earth metal)
water and the relative proportions of these four components and the chosen reaction conditions are important if the desired cylindrical zeolites of the invention with an aspect ratio of at least 0.4 are to be obtained with high crystallinity and a reduced tendency for formation of either zeolite W or amorphous products.

A preferred gel composition is:

$$2.6\text{–}2.66\ M_{2/n}O\text{:}Al_2O_3\text{:}8.8\text{–}9.7\ SiO_2\text{:}145\text{–}155\ H_2O$$

and preferably within this composition the amount of silica is within the range 9.0–9.7, more preferably 9.2–9.5, most preferably 9.2–9.4. In addition it is highly desirable for the $M_{2/n}O/SiO_2$ ratio to be at least 0.275, more preferably 0.275–0.300, most preferably 0.275–0.290.

Zeolite W tends to be formed from zeolite L crystallization gel composition. It is an advantage of this invention that the zeolite W content of the product is minimized. The zeolite W content of the product can be monitored by its X-ray diffraction pattern. A characteristic prominant line in the XRD pattern of zeolite W is at $2\theta = 12.6°$ (d = 7.09 Å), while a prominant line in the zeolite L XRD pattern is at $2\theta = 22.7°$ (d = 3.91 Å). The relative peak intensities of these peaks can be compared to determine the relative proportions of the two zeolite types, since these peaks are not obscured in mixtures of the two zeolites. It is a preferred feature that the process of the invention provides a zeolite having an XRD pattern in which the peak height ratio (d = 7.09 Å)/(d = 3.91 Å) is not greater than 0.2, more preferably not greater than 0.1. Very preferably the product is substantially free of zeolite W as evidenced by an absence of the XRD pattern of a line at a d spacing of 7.09 Å.

It is a further preferred feature that the process of the invention provide a product substantially free of amorphous and non-zeolite material.

Figure 2:
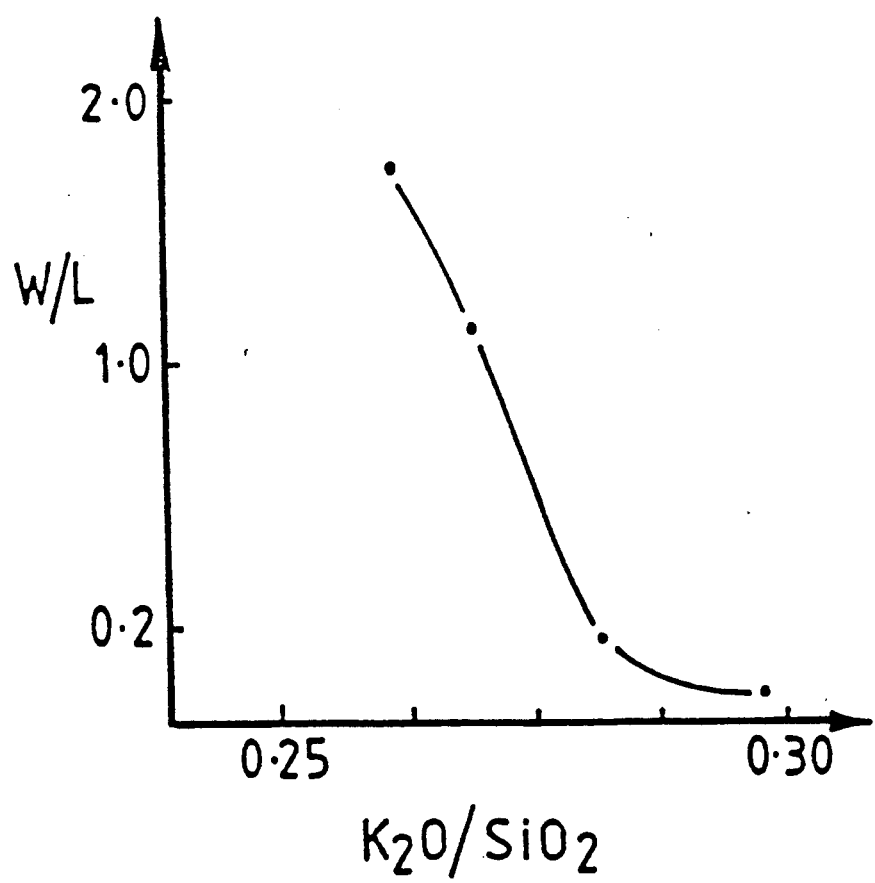

The invention will now be described in more detail, though only by way of illustration by reference to the accompanying drawings, in which:

FIG. 1 is a graph of crystallinity of zeolite L product as a function of the $K_2O/SiO_2$ molar ratio of the synthesis gel; and FIG. 2 is a graph of zeolite W to zeolite L ratio in the synthesis product as a function of the $K_2O/SiO_2$ molar ratio of synthesis gel artificially seeded with the seeds of zeolite W.

It is surprisingly been found that a highly crystalline zeolite L product with minimum zeolite W contamination may be obtained by the process of the invention, and further that the process is less liable to contamination with less crystalline product or by zeolite W as a result of minor fluctuations in the synthesis mixture. This latter advantage is particularly significant in large scale syntheses where the preparation of synthesis gels requires large volumes of reactants to be combined and the careful control of reactant amounts and/or flow rates present significant practical handling problems.

The sensitivity of the degree of crystallinity of the product to the molar ratio of $K_2O$ to $SiO_2$ in the synthesis gel for zeolite L has been investigated, as described in more detail hereinafter, and the results are shown graphically in FIG. 1. It may be seen that as the ratio decreases towards 0.25 there is a rapid reduction in the crystallinity of the product. At higher ratio there is a tendency for crystallinity to decrease slightly but the crystallinity of the product is much less sensitive to higher $K_2O/SiO_2$ ratios. In the graph the crystallinities are measured in terms of peak heights of the characteristic peaks in the X-ray diffraction spectrum and expressed as percentages of an arbitrary (100%) standard.

FIG. 2 shows the sensitivity of the zeolite W content of the product to changes in the synthesis gel mixture. As described in more detail hereinafter, zeolite L synthesis gels were seeded with zeolite W crystallites to promote zeolite W formation and the amount of zeolite W in the product was investigated for different synthesis gel mixtures. FIG. 2 shows a graph of the zeolite W/zeolite L ratio (expressed as the ratio of peak heights at 2xtheta values of 12.5° and 22.6° respectively in the X-ray diffraction pattern of the product) as a function of $K_2O/SiO_2$ molar ratio. This surprisingly, and in contrast to the prior art teaching shows that an increased $K_2O/SiO_2$ molar ratio (which may be obtained by decreasing the $SiO_2$ content of the gel) significantly increases the resistance of the process to zeolite W formation, and particularly at $K_2O/SiO_2$ ratios of 0.275 or greater, and as already shown this is an area where there is less sensitivity in the crystallinity of the product to synthesis gel mixture variation, so giving a high quality, and inherently more stable and consistent synthesis procedure.

In addition to varying the proportions of the reactants in the reaction mixture it is possible to vary the reaction conditions and in particular the crystallization temperature. By using different temperatures it is possible to deviate further from the optimum composition defined above for a crystallization temperature of 150° C. and yet still obtain the desired product. In general, within the broad reactant ratios defined for the process of the invention a higher crystallization temperature enables the silicon content to be lowered and/or the water content to be lowered and/or the potassium content (and thus the alkalinity) to be raised. By contrast operating at lower temperatures tends to decrease the nucleation rate which can be countered by lowering the alkalinity and/or by increasing the water content and/or by introducing seeds of preformed zeolite L.

In the synthesis of the zeolite according to the invention, the source of silicon for the reaction mixture is generally silica, and this is usually most conveniently in the form of a colloidal suspension of silica such as Ludox HS 40 available from E.I. Dupont de Nemours and Co. Colloidal silicon sols are preferred since they result in less contaminating phases. However other forms such as silicates may be used.

The source of aluminium may be an alumina introduced into the reaction medium as, for example, $Al_2O_3.3H_2O$, previously dissolved in alkali. However, it is also possible to introduce aluminium in the form of the metal, which is dissolved in alkali.

The potassium in the reaction mixtures is preferably introduced as potassium hydroxide. The reaction mixture may contain small quantities of other metal cations and salt forming anions as already described, but it has been found that there is an increasing tendency for other alumino-silicates to be found as the content of other ions is increased, resulting in less pure forms of the alumino-silicate of the invention. For example, excess sodium and rhubidium ions favour erionite formation, caesium ions favour pollucite formation. Thus it is highly preferred for potassium hydroxide to be the source of potassium and the source of alkalinity, and the purest products were obtained when other potassium salts were excluded.

The product of the processes described above is predominantly a potassium form of the zeolite L. By ion exchange of the product in the manner conventional to zeolite chemistry other cations such as Na or H can be introduced.

Crystallization time is related to the crystallization temperature. The crystallization is preferably carried out in the region of 150° C. and at this temperature the crystallization time may be from 24 to 96 hours, typically from 48 to 72 hours. Lower temperatures may require much longer times and may also require adjustment of alkalinity to achieve good yield of the desired product, whereas times of less than 24 hours are possible when higher temperatures are used. A time of 8 to 15 hours is typical for a temperature of greater than 200° C.

The crystallization is generally carried out in a sealed autoclave and thus at autogenous pressure. It is generally inconvenient, although possible to employ higher pressures. Lower pressure (and lower temperature) will require longer crystallization times.

Following the preparation as described above the zeolite may be separated, washed and dried in the normal manner.

The products of the processes of the invention described hereinbefore are preferably substantially free from contaminant crystalline and amorphous materials. However, in employing these products in catalytic applications it may be desired to combine them with additional crystalline or amorphous materials and this invention extends to such combinations.

We have found that the zeolite L prepared by the invention are excellent catalyst bases and may be used in conjunction with one or more catalytically-active metals in a wide variety of catalytic reactions. The particular morphology of the crystals appears to result in a particular stable base for catalytically active metals with a surprising resistance to metal catalyst deactivation. In addition, they have displayed low acidity which makes them especially suited to catalytic applications where a low acid site strength is advantageous such as aromatization.

The catalytically-active metal(s) may be, for example, a Group VIII metal such as platinum, tin, or germanium as described in U.S. Pat. No. 4,104,320, or a combination of platinum and rhenium as described in GB 2 004 764 or BE 888365. In the latter case the catalyst may for appropriate circumstances also incorporate halogen as described in U.S. Pat. No. 4,165,276, silver as described in U.S. Pat. No. 4,295,959 and U.S. Pat. No. 4,206,040, cadmium as described in U.S. Pat. No. 4,295,960 and U.S. Pat. No. 4,231,897 or sulphur as described in GB 1 600 927.

We have found a particularly advantageous catalyst composition to incorporate from 0.1 to 6.0 weight %, preferably from 0.1 to 1.5 weight % platinum or palladium, since this gives excellent results in aromatization. From 0.4 to 1.2 wt % platinum is particularly preferred, especially in conduction with the potassium form of the aluminosilicate. The invention extends to catalysts comprising the zeolitic material and a catalytically-active metal.

It may also be useful to incorporate into the catalyst of the invention one or more materials substantially inert under the conditions in which the catalyst is to be employed to act as a binder. Such binders may also act to improve the resistance of the catalyst to temperature, pressure and attrition.

The products of the invention may be used in a process for the conversion of a hydrocarbon feed in which the feed is contacted with a catalyst as described above under appropriate conditions to bring about the desired conversion. They may for example be useful in reactions involving aromatization and/or dehydrocyclization and/or isomerization and/or dehydrogenation reaction. They are particularly useful in a process for the dehydrocyclization and/or isomerization of acyclic hydrocarbons in which the hydrocarbons are contacted at a temperature of from 370° C. to 600° C., preferably from 430° C. to 550° C. with a catalyst comprising an aluminosilicate of the invention having at least 90% of the exchangeable cations M as alkali metal ions and incorporating at least one Group VIII metal having dehydrogenating activity, so as to convert at least part of the acyclic hydrocarbons into aromatic hydrocarbons.

The aliphatic hydrocarbons may be straight or branched chain acyclic hydrocarbons, and particularly paraffins such as hexane, although mixtures of hydrocarbons may also be used such as paraffin fractions containing a range of alkanes possibly with minor amounts of other hydrocarbons. Cycloaliphatic hydrocarbon such as methylcyclopentane may also be used. In a preferred aspect the feed to a process for preparing aromatic hydrocarbons and particularly benzene comprises hexanes. The temperature of the catalytic reaction may be from 370° to 600° C., preferably 430° to 550° C. and preferably pressures in excess of atmospheric are used, for example up to 2000 KPa, more preferably 500 to 1000 KPa. Hydrogen is employed in the formation of aromatic hydrocarbons preferably with a hydrogen to feed ratio of less than 10.

The process is preferably otherwise carried out in the manner described in U.S. Pat. No. 4,104,320, BE 888365 or EP 40119.

As shown in EP 96479, the use of zeolite L with cylindrical morphology enables greatly improved catalyst lifetimes to be achieved as compared to the lifetime obtained with a zeolite L, prepared according to the procedures described in the art prior to EP 96479. The invention will now be described in more detail, though only by way of illustration, in the following Preparation and Examples, with reference to the drawings.

COMPARATIVE EXAMPLE 1

Preparation of Zeolite L According to EP 96479

A synthesis gel was prepared having the following composition expressed in moles of pure oxide:

2.62 $K_2O:Al_2O_3:10SiO_2:164H_2O$

This gel was prepared as follows: 23.40 g of aluminium hydroxide was dissolved by boiling in an aqueous solution of 51.23 g of potassium hydroxide pellets (86% pure KOH) in 100.2 g water to form solution A. After dissolution any water loss was corrected. A separate solution, solution B, was prepared by diluting a 225 g of colloidal silica (Ludox HS40) with 195.0 g of water.

Solutions A and B were mixed for two minutes to form the gel, and just before the gel became fully stiff it was transferred to Teflon-lined autoclaves, preheated to 150° C. and held at that temperature for 72 hours to bring about crystallization.

The formed Zeolite L was highly crystalline with a typical Zeolite L X-ray diffraction (XRD) pattern. Scanning electron micrographs (SEM) show the product to be formed solely of well-defined cylindrical crystals having a particle size of 2 to 2.5 microns. The $SiO_2$:$Al_2O_3$ ratio in product was 6.3.$K_2O$:$Al_2O_3$ was measured as 0.99.

In large scale preparations based on this gel composition it was found that the product purity and crystallinity were badly effected by even small variations in gel composition so that a high quality zeolite L product could not be obtained.

It also appeared that the synthesis gel as described in EP 96479 is very susceptible to the formation of zeolite W, especially when the synthesis gel is contaminated with traces of W-seeds which could be present in a commercial reactor from the previous batch synthesis.

EXAMPLE 1

Effect of gel mixture on crystallinity

The procedure of the foregoing Preparation was repeated using a series of synthesis gels having compositions set out in Table 1 below.

The products from these syntheses were analysed by X-ray diffraction and the crystallinity was measured by summing the peak heights of the peaks at: (2θ±0.1) 19.3, 22.7, 24.3, 25.6, 27.2, 28.1, 29.2 and 30.7. The crystallinity for each product was then expressed as the ratio (given as percentage) of the peak height sum for the most crystalline product, and these percentages are plotted graphically versus $K_2O/SiO_2$ ratio in FIG. 1.

TABLE 1

Effect of gel mixture on crystallinity

| Gel Composition (a) | | | | Product Characteristics | |
|---|---|---|---|---|---|
| moles/mole $Al_2O_3$ | | | $K_2O/SiO_2$ | XRD | W-content |
| $K_2O$ | $SiO_2$ | $H_2O$ | Ratio | % crystallinity is most crystalline | W/L ratio |
| 2.66 | 8.4 | 144 | 0.317 | 73 | <0.03 |
| 2.65 | 8.8 | 149 | 0.301 | 85 | <0.03 |
| 2.67 | 9.3 | 156 | 0.287 | 93 | <0.03 |
| 2.66 | 10.1 | 160 | 0.263 | 100 | <0.03 |
| 2.66 | 10.3 | 162 | 0.258 | 96 | 0.03 |
| 2.64 | 10.3 | 161 | 0.256 | 95 | <0.03 |
| 2.65 | 10.4 | 161 | 0.255 | 84 | <0.03 |
| 2.64 | 10.5 | 162 | 0.251 | 55 | 0.04 |
| 2.65 | 10.6 | 164 | 0.249 | 42 | 0.06 |

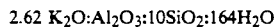
(a) gel not seed with W-seeds

EXAMPLE 2

Effect of gel mixture on zeolite W content

The procedure of the foregoing Preparation was repeated using the following gel compositions:

| | | $K_2O/iO_2$ |
|---|---|---|
| A. | 2.65$K_2O$:$Al_2O_3$:10.1$SiO_2$:160$H_2O$ | 0.262 |
| B. | 2.63$K_2O$:$Al_2O_3$:9.6$SiO_2$:156$H_2O$ | 0.274 |
| C. | 2.63$K_2O$:$Al_2O_3$:9.3$SiO_2$:153$H_2O$ | 0.283 |
| D. | 2.65$K_2O$:$Al_2O_3$:8.9$SiO_2$:156$H_2O$ | 0.298 |

Each of the gels was seeded with 100 ppm by weight of small zeolite W crystallite demonstrated to be effective to promote zeolite W formation. The XRD spectra of the products of crystallization of these gels were analyzed by measuring the ratio of the peak heights of the peaks (2 theta) at 12.5° (zeolite W) and 22.6° (zeolite L). This ratio is plotted in FIG. 2 against $K_2O/SiO_2$ molar ratio, and this figure shows the benefit of the process of the invention in giving reduced zeolite W contamination. A and B gave a very low crystallinity (33% and 38% respectively versus the standard used in Example 1) whereas C and D gave good crystallinity (73% and 76% respectively of the same standard).

COMPARATIVE EXAMPLES 2 and 3

Repeat of GB 1 393 365

Example 10 of GB 1 393 365 describes a synthesis mixture with the composition:

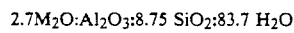
2.7M$_2$O:Al$_2$O$_3$:8.75 SiO$_2$:83.7 H$_2$O wherein K$_2$O/M$_2$O (i.e. K$_2$O+Na$_2$O)=0.8 for the preparation of zeolite AG-1. GB 1 393 365 specifies a water glass starting material for this synthesis with the composition:

Na$_2$O:4.0 SiO$_2$:42.6 H$_2$O

Howevere, the use of such a silicon source makes it impossible to comply with the other requirement of GB 1 393 365 that the water glass should be the only or major source of silicon.

A synthesis mixture of the specified composition was prepared using potassium aluminate and Ludox Hs-40 as the raw materials. A similar synthesis (not described in GB 1 393 365) was also performed using a mixture containing no sodium. The results are given in Table 1. The products had poor crystallinity, and showed no cylindrical morphology, being in the shape of clams.

COMPARATIVE EXAMPLE 4

Repetition of DT 1813099 Example 6

A synthesis gel was prepared having substantially the composition described in Example 6 of DT 1813099 (equivalent to GB 1 202 511):

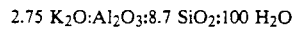
2.75 K$_2$O:Al$_2$O$_3$:8.7 SiO$_2$:100 H$_2$O 7.37 g of aluminium hydroxide were dissolved in an aqueous solution of 16.98 gms of potassium hydroxide (86% pure KOH) in 30.9 gms water to Solution A. 25.04 g of silica as Aerosil 200 were mixed with 55.4 g water for 5 minutes to form Solution B. Solutions A and B were mixed for 1 minute and the formed putty-like gel was heated in an autoclave at 140° C. for 46.5 hours.

The product was separated and dried as in Example 1. XRD and SEM showed the product to be a mixture of Zeolite W with Zeolite L. No cylindrical crystallites characteristics of the invention were observed. The procedure of DI 1813099 used drier gels than the present invention.

TABLE

|  | Gel Composition | | | | Crystallization | | Product Characteristics | | |
| --- | --- | --- | --- | --- | --- | --- | --- | --- | --- |
|  | Na$_2$O | K$_2$O | SiO$_2$ | H$_2$O | Temp. °C. | Time hrs. | Zeolite | Shape | Size (μm) |
| Comp. Ex. 2 | — | 2.70 | 8.75 | 83.7 | 135 | 25 | L | Clam | 0.5–1 |
| Comp. Ex. 3 | 0.54 | 2.16 | 8.75 | 83.7 | 135 | 25 | L | Clam | 0.5–1 |

We claim:

1. A process for the preparation of zeolite L comprising cylindrical crystallites with an aspect ratio of at least 0.4 , in which an alkaline reaction mixture comprising water, a source of silicon and a source of aluminium with a composition having the following molar ratios (expressed as oxides):

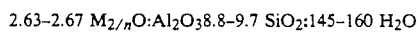
2.63-2.67 M$_{2/n}$O:Al$_2$O$_3$8.8-9.7 SiO$_2$:145-160 H$_2$O (where M is a cation of valence n or a mixture of cations and the molar ratio of M$_{2/n}$O/SiO$_2$is at least 0.275) is heated to a temperature of at least 75° C. to form the desired zeolite L product.

2. A process as claimed in claim 1, in which the reaction mixture has the composition:

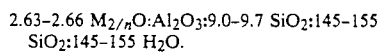
2.63-2.66 M$_{2/n}$O:Al$_2$O$_3$:9.0-9.7 SiO$_2$:145-155 SiO$_2$:145-155 H$_2$O.

3. A process as claimed in claim 2, in which the reaction mixture has the composition:

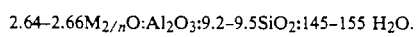
2.64-2.66M$_{2/n}$O:Al$_2$O$_3$:9.2-9.5SiO$_2$:145-155 H$_2$O.

4. A process as claimed in any of claims 1 to 3, in which the molar ratio of M$_{2/n}$O/SiO$_2$ is 0.275-0.290.

5. A process as claimed in any one of claims 1 to 4, in which the temperature is from 120° C. to 225° C.to 225 C.

6. A process as claimed in any one of claims 1 to 5, in which cation M is potassium.

7. A catalyst comprising a zeolite prepared by a process as claimed in any one of claims 1 to 6 and one or more catalytically-active metals.

8. A catalyst as claimed in claim 7, comprising from 0.1 to 1.5 weight % platinum.

* * * * *